United States Patent [19]

Glassy et al.

[11] Patent Number: 4,761,377
[45] Date of Patent: Aug. 2, 1988

[54] HUMAN-HUMAN HYBRID CELL LINES THAT PRODUCE ANTIBODIES AGAINST ANTIGENIC DETERMINANTS ON CANCER CELLS

[75] Inventors: Mark C. Glassy; Charles Surh, both of San Diego, Calif.

[73] Assignee: The Regents of the University of California, Berkeley, Calif.

[21] Appl. No.: 661,110

[22] Filed: Oct. 15, 1984

[51] Int. Cl.$^4$ .................. C12N 5/00; C07K 15/04; A61K 39/395

[52] U.S. Cl. .................. 435/240.27; 435/68; 435/70; 435/172.2; 935/100; 530/387; 424/85

[58] Field of Search .................. 424/1.1, 9, 85; 435/7, 435/29, 68, 70, 172.2, 240, 241, 188, 948, 240.27; 935/89, 100, 107, 108, 110; 436/548, 519, 63, 64, 804, 813; 514/2; 530/387

[56] References Cited

U.S. PATENT DOCUMENTS

| | | | |
|---|---|---|---|
| 4,434,230 | 2/1984 | Ritts, Jr. | 435/240 |
| 4,451,570 | 5/1984 | Royston | 435/240 |
| 4,464,465 | 8/1984 | Lostrom | 435/240 |
| 4,522,918 | 6/1985 | Schlom et al. | 435/68 |
| 4,529,694 | 7/1985 | Lazarus et al. | 435/68 |

FOREIGN PATENT DOCUMENTS

8201461 5/1982 PCT Int'l Appl. .................. 435/240

OTHER PUBLICATIONS

Schlom, J. et al., Proc. Natl. Acad. Sci., USA, 77(11): 6841–6845, (11-1980).
Wunderlich, D. et al., Eur. J. Cancer Clin. Oncol., 17(7): 719–730, (1981).
Gilliland, D. G. et al., Proc. Natl. Acad. Sci., USA, 77(8): 4539–4543 (8-1980).
Sikora, K. et al., *Monoclonal Antibodies and Cancer*, B. D. Boss et al., eds., Academic Press, Orlando (1983), pp. 171–180.
Edwards, P. A. W. et al., *Monoclonal Antibodies and Cancer*, Ibid., pp. 181–184.
Glassy, M. C. et al., Ibid., pp. 163–170.
Heitzmann, J. G. et al., Ibid., pp. 157–162.
Foon, K. A. et al., Ibid., pp. 143–156.
Olsson, L. et al., Methods in Enzymology, 92:3–16, (1983).
Kaplan, H. A. et al., *Monoclonal Antibodies in Clinical Medicine*, McMichael, A. J. et al., eds., Academic Press, London (1982), pp. 17–35.
Handley, H. H. et al., Immunobiology, 163: 2–4, (1982).
Glassy, M. C. et al., Proc. Natl. Acad. Sci., USA, 80 (20): 6327–6331 (1983).
Glassy, M. C. et al., Journal of Immunological Methods, 58: 119–126 (3-1983).
Cole, S., et al., "Human Monoclonal Antibodies." *Molecular and Cellular Biochemistry.* 1984, 82:109–120.
Heitzman, J., and M. Cohn. "The WI-L2-729-HF$_2$ Human Hybridoma System." *Molecular Biology and Medicine.* 1983, 1:235–243.
Hagiwara, H., and G. Sato. "Human X Human Hybridoma Producing Monoclonal Antibody against Autologous Cervical Carcinoma." *Molecular Biology and Medicine.* 1983, 1:245–252.

Primary Examiner—Margaret Moskowitz
Attorney, Agent, or Firm—Brown, Martin, Haller & Meador

[57] ABSTRACT

Human-human hybrid cell lines that synthesize and secrete monoclonal antibodies against antigenic determinants on cancer cells, generated by fusing a human lymphoblastoid B cell line to human lymphocytes, and therapeutic and diagnostic uses of the monoclonal antibodies in both cancer treatment and research is disclosed.

4 Claims, 2 Drawing Sheets

HUMAN-HUMAN HYBRID CELL LINES THAT PRODUCE ANTIBODIES AGAINST ANTIGENIC DETERMINANTS ON CANCER CELLS

ACKNOWLEDGEMENT

This invention was made with Government support under Grant No. CA-32047-01 with the National Institutes of Health and the University of California. The Government has certain rights in this invention.

FIELD OF THE INVENTION

This invention relates to human-human hybrid cell lines that produce monoclonal antibodies against antigenic determinants on cancer cells, particularly carcinoma of the vulva, stomach, colon, lung and cervix.

BACKGROUND OF THE INVENTION

In the past few years there has been considerable research effort focused on developing immunotherapeutic regimes for treating cancer. In nearly all of these studies antibodies against tumor-associated antigens have been utilized to treat patients suffering from various malignant disorders, unfortunately, with little success. There appear to be four major reasons for the lack of success, two being: first, tumor-associated antigens are difficult to identify; and, second, it is technically difficult and laborious to prepare homogeneous antibody that recognize tumor-associated antigens. The latter difficulty has been largely circumvented by the development of the hybridoma technique of Kohler and Milstein (Nature, Vol. 256, p.495, 1975), which allows for the unlimited production of monoclonal antibody. As for identifying tumor-associated antigens, there is at present no sure way to identify antigens restricted to cancer cells.

The third problem which must be surmounted when devising an immunotherapeutic regime for treatment of cancer is to prevent an immune reaction against the immunotherapeutic agent, that is, against the antibodies directed to the tumor-associated antigen. This problem is amenable to solution by employing human antibodies generated by modification of the basic Kohler and Milstein technique, as described by Glassy et al in *Monoclonal Antibodies and Cancer,* eds. Boss et al(1983), Academic Press, and Glassy et al, Proc. Natl. Acad. Sci. USA 80:6327 (1983). Human monoclonal antibodies, when injected into a patient bearing a tumor, recognize and bind to the tumor by binding to the tumor-associated antigen. Since the antibody is of human origin it will not be "seen" as a foreign substance by the patient's immune system and is therefore immunologically blind.

Fourth, most of the human monoclonal antibodies generated to date are of the IgM class. This class of antibody, although useful for a variety of in vitro studies, is not as clinically useful as antibody of the IgG class. The generation of one class of monoclonal antibody over another is, at present, poorly understood, and hence not reproducible.

Despite the advent of methods for generating human-human hydridomas, there have been to date few human hydridomas that secrete monoclonal antibodies against tumor-associated antigens. As described by Handley, Royston and Glassy in *Intercellular Communication in Leucocyte Function,* Proceedings of the 15th International Leucocyte Culture Conference; Wiley Interscience, N.Y.; p. 617, 1983, human monoclonal antibodies have, however, been generated to date against lung tumors, gliomas, melanomas, and tumors of the prostate and mammary glands. The reason for the paucity of such potentially powerful therapeutic agents is partly due to the technique used to generate the hybridomas. While the general technique is understood conceptually, there are many factors which are poorly understood and yet are responsible for ultimately yielding a human hybridoma cell line. Thus, in essence, there is a great degree of unpredictability in generating human hybridomas that either secrete monoclonal antibody against tumor-associated antigens, or that secrete monoclonal antibody of the preferred IgG class. Indeed there is no assurance prior to attempting to generate a hybridoma that it will, in fact, be obtained at all.

At present immunotherapy has been of little use in treating or diagnosing cancers of the vulva, stomach or other organs for the above mentioned reasons. Thus the establishment of human-human hybrid cell lines that secrete IgG monoclonal antibodies against tumor-associated antigens is sorely needed.

SUMMARY OF THE INVENTION

According to this invention, human-human hybrid cell lines, i.e., hybridomas, that synthesize and secrete human IgG monoclonal antibodies are generated by fusing lymphocytes isolated from a regional draining lymph node from a patient containing carcinoma of the vulva to a drug-resistant human lymphoblastoid B cell line.

DETAILED DESCRIPTION OF THE INVENTION

Figure 1:
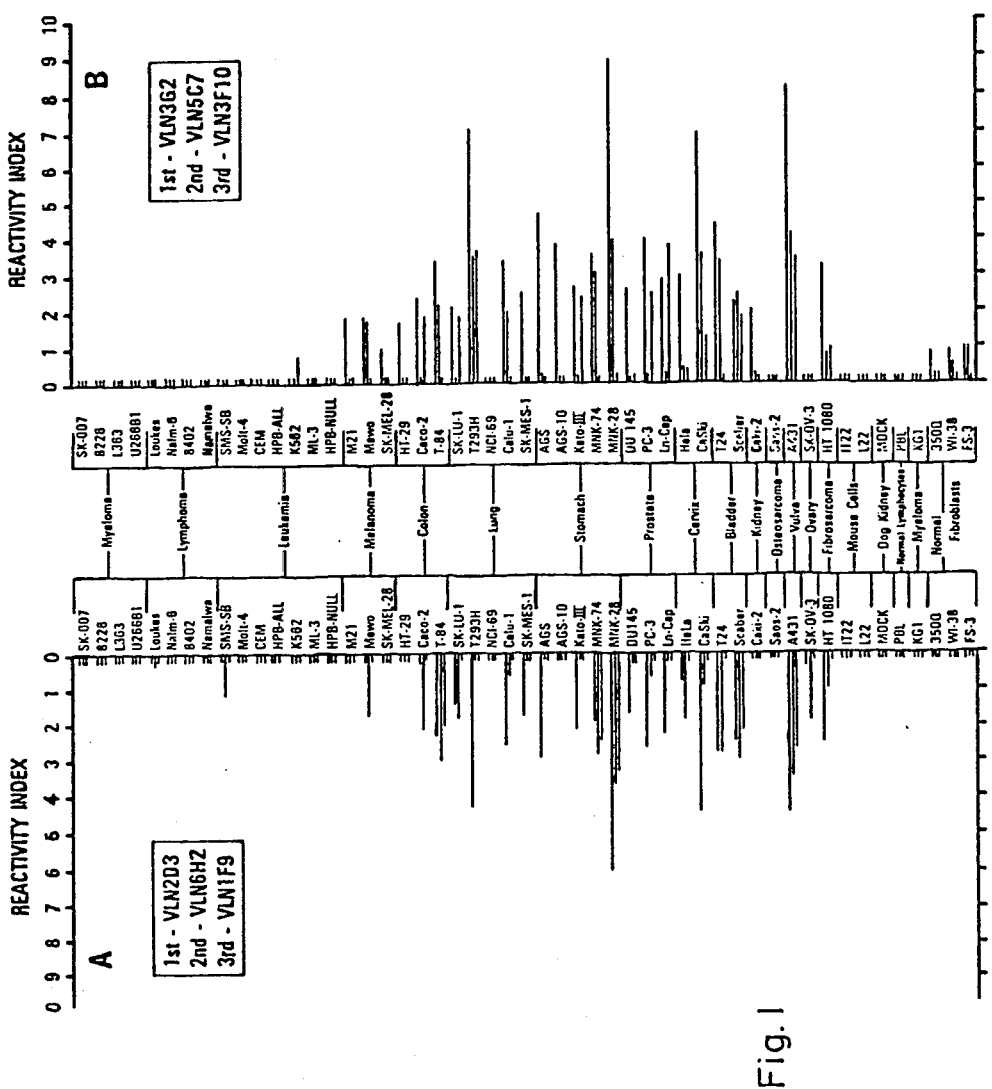
FIG. 1 shows the reactivity index of human monoclonal antibodies against various cancers.

In accordance with the present invention B cell lymphocytes are isolated from a patient that exhibits a tumor burden. The B cells are isolated by surgical techniques from lymph nodes of the patient, particularly from regional draining lymph nodes near the tumor mass. Alternatively, B cells can be isolated from other lymphoid organs, such as spleen, tonsils and peripheral blood. Regardless of the organ used to obtain the B cells, the latter are prepared in a form suitable for hybridoma formation. To generate hybridomas using lymph nodes as a source of lymphocytes, a suitable procedure is to obtain a patients lymph nodes cells resulting from surgery, tease them apart in a suitably isotonic buffered solution with forceps to release individual lymphocytes. Lymph node cells are then fused by combining them with a suitable fusion partner cell, such as U.C. 729-6 (on deposit with the American Type Culture Collection, with accession no. CRL 8061) at a ratio of about 2 lymphocytes to 1 U.C. 729-6 cell. The latter takes place in a solution of about 35% polyethylene glycol in a suitably buffered isotonic medium, particularly Roswell Memorial Park Institute 1640 medium (RMPI-1640). The mixture of cells is then suspended in an appropriate selective media, particularly HAT medium containing about 10% fetal calf serum, and placed in wells at about $10^5$ cells per well, and permitted to grow for a sufficient time. The overnight culture period increases the efficiency of hybridoma formation but is not absolutely crucial if a low yield of hybridomas is acceptable.

In order to obtain human hybrids the B lymphocytes must be fused to a human cell line that exhibits a drug selectable marker; generally such cell lines are of lymphoblastoid origin. Alternatively the human cell line could be selected against based on its ability to exhibit temperature sensitive inhibition of growth. The cell line is maintained in RPMI-1640 culture media prior to fusion.

To form human-human hybrid cell lines the lymph node lymphocytes are mixed with the lymphoblastoid cell line; usually an equal or ten-fold greater number of lymph node lymphocytes are combined with the lymphoblastoid cell line. The two cell types are pelleted to the bottom of a centrifuge tube and fused for an appropriate time with a chemical fusing agent, particularly polyethylene glycol (PEG). Alternatively, fusion can be accomplished by electro cell fusion or by viruses, particularly Sendai and Abelson. Fused cells were then plated in media containing drugs which selectively kill unfused lymphoblastoid cells. The hybrid cell lines which grow up, generally within 10 to 20 days, are screened for human antibody production by assaying for antibodies present in the culture media using one of many immunoassay methods, but particularly that described by Glassy et al in the Journal of Immunological Methods, Vol. 58, p. 119 (1983) example, a small volume of an affinity purified goat anti-human antibody, or a target cell can be immobilized on a suitable surface, particularly useful are matrices made of glass fibers. These can be positioned in an immunofiltration manifold, which can be purchased from B and P Scientific, San Diego, Calif., catalog no. BP107. The latter is particularly convenient as it permits washing of material bound to the glass fiber substrate. The glass fiber substrate material containing bound affinity purified goat anti-human antibody, or target cells, is washed to remove interfering materials, and then a suitable amount of hybrodoma supernatent which is sought to be tested for human antibody is incubated with the substrate material for 30 minutes at room temperature. The filters are washed and then incubated with a suitable detector molecule such as horseradish peroxidase conjugated goat-anti-human antibody for an additional 30 minutes. The filters can be further washed to remove unbound labeled antibody, and then incubated with a suitable substrate such as ortho-phenylene diamine in and an appropriate buffer. The result is a colored solution present in wells having hybridoma antibodies. The latter can be visually detected, or detected and quantified in a micro-Elisa reader such as, for example, that manufactured by Dynatek (Alexandria, Va.). Prior to reading the wells, a suitable amount of acid solution, such as sulfuric acid is added to stop the color reaction, and then the wells are read at 492 nM. It will be apparent to those skilled in the art that the gones that encode antibody in the hybridoma cell lines can, by DNA recombinant techniques, be transferred to other cell types, and that the latter can act as a source of monoclonal antibody.

Monoclonal antibodies present in the culture media of the hybridomas were purified by standard techniques, including exclusion and affinity chromotographic procedures and were assayed to determine which immunoglobuline class they belong to, and their cell type specificities. Antibody class determination was conducted by standard techniques using the appropriate antisera, and found to be of the IgG class as described by Glassy et al in the *Journal of Immunological Methods*, Vol. 58, p. 119 (1983). To determine the cell type specificity both normal and cancer tissue was assayed on frozen sections using indirect immunofluorescent staining techniques, and cell lines by an enzyme immunoassay.

The monoclonal antibodies selectively react with non-hematopoietic human cancers, particularly tumors of the prostate, stomach, vulva and to a lessor degree with cervix, colon, lung and breast. None of the monoclonal antibodies react with the normal tissues tested. It is important to note that while the monoclonal antibodies have been found to react only with the aforementioned tumors, it is to be anticipated that they will react with other tumors that express the antigen recognized by the monoclonal antibody.

Monoclonal antibodies generated as described above inhibit the growth of tumor cells in vitro. This is accomplished by adding monoclonal antibodies in the range of 5-50 micrograms/ml to tumor cells and measuring their growth rate over several days. It is to be anticipated that monoclonal antibodies generated by this invention will inhibit the growth of a wide variety of other tumor cell types, and furthermore that fragments, or combinations of antibody heavy and light chains will inhibit tumor growth as the antigen combining site of the molecule is retained.

The example disclosed below represents the best embodiment of the invention as contemplated. However, it is to be understood that various changes and modifications may be made without departing from the spirit of the invention.

EXAMPLE I

Establishment of human-human hybridomas

In order to generate human monoclonal antibodies it is first necessary to establish the hybrid cell lines termed hybridomas that secrete them. This is accomplished by chemically fusing human lymphpocyte B cells to a human lymphoblastoid cell line. Lymphocytes are obtained from regional draining lymph nodes of a patient with a carcinoma of the vulva. Lymph nodes were obtained within three hours after removal by surgery. The lymph nodes were teased apart in Rosewell Park Memorial Institute 1640 (RPMI-1640) so as to release the lymphocytes which were separated from large pieces of tissue debris by letting the debris sediment under unit gravity. The lymphocytes that remained in suspension were cultured overnight at 37° C. in an atmosphere of 5% $CO_2$/95% air in RPMI-1640 media supplemented with 10% fetal calf serum and 2 mM L-glutamine. The next day the lymphocytes were counted and mixed in ratio of 2:1 with the human lymphoblastoid cell line UC 729-6. The cell mixture was washed in RPMI media minus serum by centrifugation at 150×g to yield a pellet composed of lymphocytes and lymphoblastoid cells. The supernatant was completely aspirated from the cell pellet and 1.0 ml of 35% polyethylene glycol 1500(BDH; lot no. 6229890) was added dropwise over a 30-sec interval to a dry cell pellet and allowed to stand at room temperature for 2 min. At 2-min intervals, the following volumes of serum-free RPMI 1640 medium were added: 1.0 ml, 2.0 ml, 4.0 ml, and 8.0 ml. After addition of the final 8.0-ml volume of medium, the cells were spun at 300×g for 5 minutes, the supernatant was aspirated, and the pellet was carefully suspended in medium supplemented with 10% fetal calf serum, glutamine, and 0.2 mM hypoxanthine/0.2 μM amethopterin/32 μM thymidine (HAT). Cells were plated at $1.0 \times 10^5$ per well in Costar 96-well microtiter plates without the use of feeder layer cells. Since the lymphoblastoid cell line UC729-6 is resistant to growth in 6-thioguanine, it lacks the enzyme hypoxanthine-guanine phosphoribosyl tranferase. Consequently, unfused UC729-6 cells die in HAT media. Hybridomas, however, survive and grow since the enzymes necessary for survival in HAT media are derived from the lymph node lymphocytes.

EXAMPLE II

Detection of monoclonal antibodies produced by human-human hybridomas

Within 10–20 days after the lymphocytes are fused to the lymphoblastoid cell line and plated into microtiter plates, hybridoma growth is apparent and the media was assayed for human antibody production. Media was assayed for the presence of monoclonal antibodies by an enzyme linked immunoabsorbant assay previously described by Glassy et al in the *Journal of Immunological Methods,* Vol. 58, p.119 (1983). The assay was conducted by adding 50 μl of an affinity purified, class specific goat antihuman Ig antibody so as to immobilize it in an immunofiltration manifold. Each well of the manifold was washed three times with 0.3% gelatin in phosphate-buffered saline before the addition of 50 microlitres of hybridoma media supernatant. The latter was incubated for 30 minutes at room temperature, and then the filters washed again three times with phosphate-buffered saline. A second incubation followed with 50 microlitres of a class-specific horseradish peroxidase-conjugated goat anti-human Ig for an additional 30 minute period. Finally, filters are washed again three times and incubated with 150 microlitres of a 400 microgram/ml solution of orthophenylenediamine in citrate buffer. 100 microlitres from each well were then transferred to a 96 well microtiter plate containing 50 microlitres of 2.5 molar sulphuric acid and the optical density at 490 nanometers read on a Dynatech microELISA reader. Media from wells that gave an optical density above control levels, $\geq$ 2-fold over background, were considered positive for human monoclonal antibody, and the hybridomas in the corresponding cell culture wells were grown up and cloned by limiting dilution. As a consequence of this procedure five hybridomas producing IgG monoclonal antibodies were identified and termed VLN3G2, VLN5C7, VLN6H2, VLN1F9, and VLN3F10. The hybridomas are on deposit with the American Type Culture Collection, and have the following respective deposit numbers; VLN3G2/HB8636, VLN567/HB8634, VLN6H2/HB8633, VLN1F9/HB8635, and VLN3F10/HB8632.

EXAMPLE III

Identification of the cancer cell type specificity of the human monoclonal antibodies.

The cancer cell type specificity of the human monoclonal antibodies was determined by one of two methods; either cancer cell lines or frozen sections of cancer tissue were assayed for antibody binding. Cancer cell lines used in the assay are shown in FIG. 1. Antibody binding to the cell lines was determined using the identical materials and methods described in Example II, that is by ELISA assay, with the exception that $2 \times 10^5$ target cells/well were immobilized on the filtration manifold. Monoclonal antibodies secreted by the hybridomas VLN3G2, VLN5C7, VLN1F9, VLN3F10 and VLN6H2 and their reactivity with a large panel of cell lines is shown in FIG. 1. Cells were considered reactive with the human monoclonal antibodies if the Reactivity Index was 2.0 or higher. Reactivity Index is defined as the number of times the irrelevant or control IgG value goes into the test human IgG value.

Screening the monoclonal antibodies on frozen sections was performed on six to eight micron thick tissue sections cut at −20° C., and incubated with the monoclonal antibody for 1–2 hours, the section was washed to remove unbound antibody, and then reincubated with a fluorescent labelled antihuman antibody. The latter can be goat antihuman, rabbit antihuman or antihuman antibodies from other species. The second incubation was for 1–2 hours, followed by thorough washing, and visualization of immunofluorescent staining with an immunofluorescent microscope.

FIG. 1 shows the reactivity index of the monoclonal antibodies with various tumor cell lines and tumor tissue. For comparative purposes the reactivity index of monoclonal antibodies produced by the hybridoma VLN2D3 is also shown. VLN2D3 secretes a monoclonal antibody hybridoma that primarily recognizes vulva tissue or developmentally related tissues.

EXAMPLE IV

Inhibition of cancer cell growth by human monoclonal antibodies.

Figure 2:
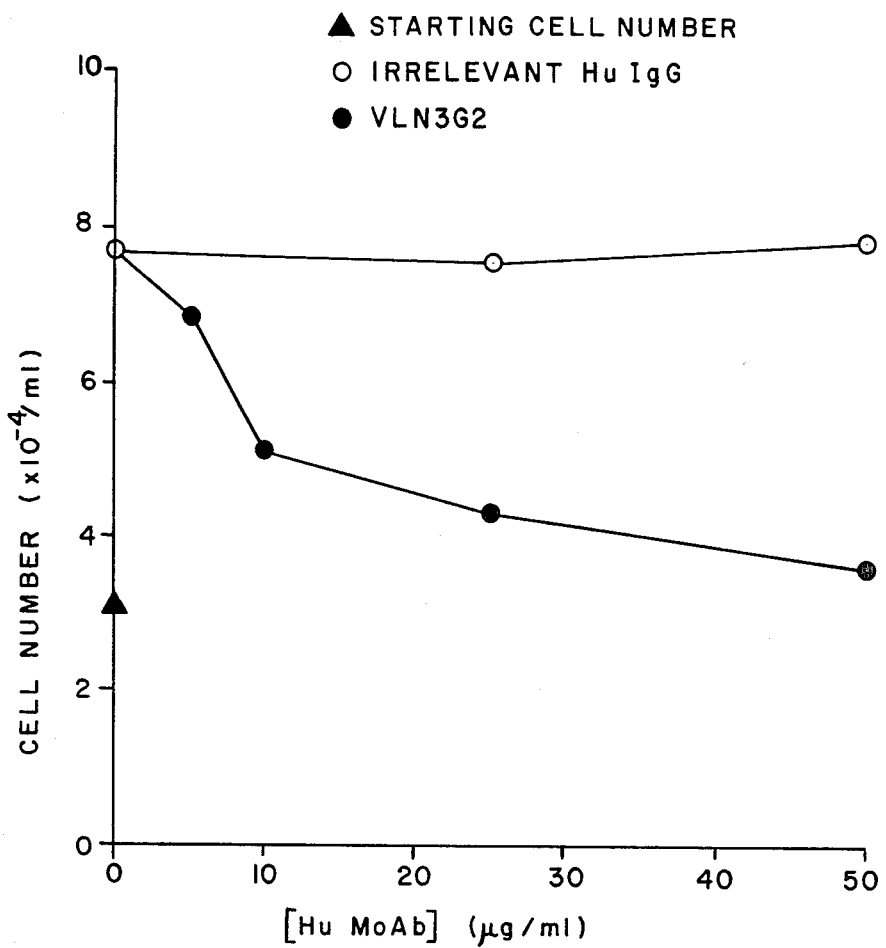
FIG. 2 shows the growth inhibitory effect of human monoclonal antibody on the tumor cell line, A431.

Monoclonal antibody VLN3G2 inhibits the growth of cancer cells as assessed by the ability of VLN3G2 to inhibit the growth of the vulva carcinoma cell line A431. FIG. 2 shows that between 5–50 micrograms/ml of monoclonal antibody there is a marked inhibition of the growth rate of the cell line. About $3 \times 10^4$ cells was seeded in Rosewell Park Memorial Institute-1640 media supplemented with 10% fetal calf serum at time 0 with monoclonal antibody. Cell number was determined three days later.

EXAMPLE V

Identification of protein antigens recognized by the human monoclonal antibodies.

Human monoclonal antibodies VLN3G2, VLN5C7 and VLN6H2 recognize epitopes on a 78,000 molecular weight surface protein present on the cell line A431 and a 66,000 molecular weight protein present on the oat cell lung carcinoma cell line, T293H. This was determined by metabolically labelling the cell lines in Rosewell Park Memorial Institute-1640 media supplemented with 10% fetal calf serum and $^{35}S$ methionine. The Rosewell Park Memorial Institute-1640 media contained 10% of its normal complement of methionine, and 1–5 microcuries of $^{35}S$ methionine per millimeter. The cell lines were labelled overnight with $^{35}S$ methionine, the next day washed three times with phosphate buffered saline and then lysed in NP-40, a non-ionic detergent, and the non-soluble material pelleted by low speed centrifugation. 30 micrograms of the monoclonal antibodies were added to the cell extract supernatant and the isolated immunoprecipitate subjected to tube gel polyacrylamide gel electrophoresis. Gels were sliced into 2 mm sections and radioactivity was assessed by standard scintillation chromatography. The apparent molecular weight values were obtained from a standard curve. The isoelectric point of the antigen isolated from the A431 cells is 5.82; the isoelectric point of the antigen isolated from the T293H cells is 4.96.

We claim:

1. Human anticancer monoclonal antibodies synthesized by hybridoma cell lines produced by fusing human lymph node cells from a patient suffering from carcinoma of the vulva and a human cell line that is sensitive to growth in drug supplemented media, said anticancer monoclonal antibodies being selected from the group consisting of VLN3F10 with American Type Culture Collection No. HB 8632, VLN6H2 with American Type Culture Collection No. HB 8633, VLN5C7 with American Type Culture Collection No. HB 8634, and VLN1F9 with American Type Culture Collection No. HB 8635.

2. Hybridoma cell lines that produce human monoclonal antibodies formed by fusing human lymph node cells from a patient suffering from carcinoma of the vulva with a human cell line that is sensitive to growth in drug supplemented media, said hybridoma cell lines being selected from the group consisting of VLN3F10 with American Type Culture Collection No. HB 8632, VLN6H2 with American Type Culture Collection No. HB 8633, VLN5C7 with American Type Culture Collection No. HB 8634, VLN1F9 with American Type Culture Collection No. HB 8635, and VLN3G2 with American Type Culture Collection No. HB 8636.

3. Human anticancer monoclonal antibodies synthesized by hybridoma cell line VLN3G2 on deposit with American Type Culture Collection, Accession No. HB 8636, produced by fusing human lymph node cells from patients with carcinoma of the vulva and a human cell line that is sensitive to growth in drug supplemented media.

4. Hybridoma cell line VLN3G2 on deposit with American Type Culture Collection, Accession No. HB 8636, that produces human monoclonal antibodies formed by fusing human lymph node cells from a patient suffering from carcinoma of the vulva with a human cell line that is sensitive to growth in drug supplemented media.

* * * * *